US012697464B2

(12) United States Patent
Sepulveda et al.

(10) Patent No.: US 12,697,464 B2
(45) Date of Patent: Aug. 4, 2026

(54) REINFORCED CATHETER TIP VIA ROLLER EXTRUSION

(71) Applicant: Bard Access Systems, Inc., Salt Lake City, UT (US)

(72) Inventors: Juan Sepulveda, Centerville, UT (US); Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 859 days.

(21) Appl. No.: 17/980,455

(22) Filed: Nov. 3, 2022

(65) Prior Publication Data

US 2023/0132903 A1     May 4, 2023

Related U.S. Application Data

(60) Provisional application No. 63/275,768, filed on Nov. 4, 2021.

(51) Int. Cl.
A61M 25/00          (2006.01)

(52) U.S. Cl.
CPC ...... A61M 25/001 (2013.01); A61M 25/0069 (2013.01)

(58) Field of Classification Search
CPC ............ A61M 25/001; A61M 25/0069; A61M 25/0067; A61M 25/0606; A61M 25/0009;
(Continued)

(56) References Cited

U.S. PATENT DOCUMENTS

| 1,013,691 A | 1/1912 | Shields |
| 1,906,678 A | 5/1933 | Wappler |

(Continued)

FOREIGN PATENT DOCUMENTS

| EP | 0730880 A1 | 9/1996 |
| EP | 2061385 A1 | 5/2009 |

(Continued)

OTHER PUBLICATIONS

PCT/US2022/047179 filed Oct. 19, 2022 International Preliminary Report on Patentability dated Apr. 23, 2024.
(Continued)

*Primary Examiner* — Jason L Vaughan
*Assistant Examiner* — Amanda Kreiling
(74) *Attorney, Agent, or Firm* — Rutan & Tucker LLP

(57)          ABSTRACT

With smaller gauge catheters, forming distal tip structures, termed "tipping," can be increasingly challenging. The thin wall-thicknesses of these small gauge catheters provide a reduced cross-sectional surface area with which to couple the distal tip structure to. This increases the risk of failure of the device either during manufacture or during use. To address the foregoing, embodiments include forming and placing a spiral plug within a lumen of a proximal section of the catheter. The spiral plug co-operates with the catheter to provide an increased wall thickness and an increased cross-sectional surface area with which to couple a distal tip structure thereto. Further the spiral plug can align the lumen of the catheter body with a lumen of the distal tip structure. The spiral plug can be sacrificial and provide increased material across the joint, mitigating joint failure.

11 Claims, 7 Drawing Sheets

(58) Field of Classification Search

CPC .............. A61M 25/00; A61M 25/0043; A61M 25/0023; A61M 25/0113; A61M 25/0068; A61M 25/007

See application file for complete search history.

(56) References Cited

U.S. PATENT DOCUMENTS

| | | |
|---|---|---|
| 3,225,762 A | 12/1965 | Guttman |
| 3,710,781 A | 1/1973 | Huthcins, IV et al. |
| 3,890,976 A | 6/1975 | Bazell et al. |
| 4,205,675 A | 6/1980 | Vaillancourt |
| 4,270,535 A | 6/1981 | Bogue et al. |
| 4,292,970 A | 10/1981 | Hession, Jr. |
| 4,468,224 A | 8/1984 | Enzmann et al. |
| 4,525,157 A | 6/1985 | Vaillancourt |
| 4,581,019 A | 4/1986 | Curelaru et al. |
| 4,661,300 A | 4/1987 | Daugherty |
| 5,004,455 A | 4/1991 | Greenwood et al. |
| 5,017,259 A | 5/1991 | Kohsai |
| 5,040,548 A | 8/1991 | Yock |
| 5,057,073 A | 10/1991 | Martin |
| 5,112,312 A | 5/1992 | Luther |
| 5,120,317 A | 6/1992 | Luther |
| 5,135,599 A | 8/1992 | Martin et al. |
| 5,167,623 A | 12/1992 | Cianci et al. |
| 5,188,593 A | 2/1993 | Martin |
| 5,195,962 A | 3/1993 | Martin et al. |
| 5,207,650 A | 5/1993 | Martin |
| 5,267,958 A | 12/1993 | Buchbinder et al. |
| 5,295,970 A | 3/1994 | Clinton et al. |
| 5,306,247 A | 4/1994 | Pfenninger |
| 5,328,472 A | 7/1994 | Steinke et al. |
| 5,350,358 A | 9/1994 | Martin |
| 5,368,567 A | 11/1994 | Lee |
| 5,378,230 A | 1/1995 | Mahurkar |
| 5,380,290 A | 1/1995 | Makower et al. |
| 5,389,087 A | 2/1995 | Miraki |
| 5,439,449 A | 8/1995 | Mapes et al. |
| 5,443,457 A | 8/1995 | Ginn et al. |
| 5,489,271 A | 2/1996 | Andersen |
| 5,573,520 A | 11/1996 | Schwartz et al. |
| 5,645,528 A | 7/1997 | Thome |
| 5,683,370 A | 11/1997 | Luther et al. |
| 5,690,613 A | 11/1997 | Verbeek |
| 5,718,678 A | 2/1998 | Fleming, III |
| 5,772,636 A | 6/1998 | Brimhall et al. |
| 5,810,789 A * | 9/1998 | Powers .............. A61M 25/0075 604/247 |
| 5,885,251 A | 3/1999 | Luther |
| 5,908,409 A | 6/1999 | Rinehart et al. |
| 5,919,164 A | 7/1999 | Andersen |
| 5,947,940 A | 9/1999 | Beisel |
| 5,957,893 A | 9/1999 | Luther et al. |
| 6,206,849 B1 | 3/2001 | Martin et al. |
| 6,332,877 B1 | 12/2001 | Michels |
| 6,475,187 B1 | 11/2002 | Gerberding |
| 6,551,290 B1 | 4/2003 | Elsberry et al. |
| 6,606,515 B1 | 8/2003 | Windheuser et al. |
| 6,716,228 B2 | 4/2004 | Tal |
| 6,726,659 B1 | 4/2004 | Stocking et al. |
| 6,819,951 B2 | 11/2004 | Patel et al. |
| 6,821,287 B1 | 11/2004 | Jang |
| 6,926,692 B2 | 8/2005 | Katoh et al. |
| 6,962,575 B2 | 11/2005 | Tal |
| 6,994,693 B2 | 2/2006 | Tal |
| 6,999,809 B2 | 2/2006 | Currier et al. |
| 7,025,746 B2 | 4/2006 | Tal |
| 7,029,467 B2 | 4/2006 | Currier et al. |
| 7,037,293 B2 | 5/2006 | Carrillo et al. |
| 7,074,231 B2 | 7/2006 | Jang |
| 7,141,050 B2 | 11/2006 | Deal et al. |
| 7,144,386 B2 | 12/2006 | Korkor et al. |
| 7,311,697 B2 | 12/2007 | Osborne |
| 7,364,566 B2 | 4/2008 | Elkins et al. |
| 7,377,910 B2 | 5/2008 | Katoh et al. |
| 7,390,323 B2 | 6/2008 | Jang |
| D600,793 S | 9/2009 | Bierman et al. |
| D601,242 S | 9/2009 | Bierman et al. |
| D601,243 S | 9/2009 | Bierman et al. |
| 7,594,911 B2 | 9/2009 | Powers et al. |
| 7,691,093 B2 | 4/2010 | Brimhall |
| 7,722,567 B2 | 5/2010 | Tal |
| D617,893 S | 6/2010 | Bierman et al. |
| D624,643 S | 9/2010 | Bierman et al. |
| 7,819,889 B2 | 10/2010 | Healy et al. |
| 7,857,788 B2 | 12/2010 | Racz |
| D630,729 S | 1/2011 | Bierman et al. |
| 7,909,797 B2 | 3/2011 | Kennedy, II et al. |
| 7,909,811 B2 | 3/2011 | Agro et al. |
| 7,922,696 B2 | 4/2011 | Tal et al. |
| 7,938,820 B2 | 5/2011 | Webster et al. |
| 7,967,834 B2 | 6/2011 | Tal et al. |
| 7,985,204 B2 | 7/2011 | Katoh et al. |
| 8,073,517 B1 | 12/2011 | Burchman |
| 8,105,286 B2 | 1/2012 | Anderson et al. |
| 8,192,402 B2 | 6/2012 | Anderson et al. |
| 8,202,251 B2 | 6/2012 | Bierman et al. |
| 8,206,356 B2 | 6/2012 | Katoh et al. |
| 8,372,107 B2 | 2/2013 | Tupper |
| 8,377,006 B2 | 2/2013 | Tal et al. |
| 8,454,577 B2 | 6/2013 | Joergensen et al. |
| 8,585,858 B2 | 11/2013 | Kronfeld et al. |
| 8,657,790 B2 | 2/2014 | Tal et al. |
| 8,672,888 B2 | 3/2014 | Tal |
| 8,696,645 B2 | 4/2014 | Tal et al. |
| 8,784,362 B2 | 7/2014 | Boutilette et al. |
| 8,827,958 B2 | 9/2014 | Bierman et al. |
| 8,876,704 B2 | 11/2014 | Golden et al. |
| 8,882,713 B1 | 11/2014 | Call et al. |
| 8,900,192 B2 | 12/2014 | Anderson et al. |
| 8,900,207 B2 | 12/2014 | Uretsky |
| 8,915,884 B2 | 12/2014 | Tal et al. |
| 8,956,327 B2 | 2/2015 | Bierman et al. |
| 9,023,093 B2 | 5/2015 | Pal |
| 9,138,252 B2 | 9/2015 | Bierman et al. |
| 9,180,275 B2 | 11/2015 | Helm |
| 9,265,920 B2 | 2/2016 | Rundquist et al. |
| 9,272,121 B2 | 3/2016 | Piccagli |
| 9,522,254 B2 | 12/2016 | Belson |
| 9,554,785 B2 | 1/2017 | Walters et al. |
| 9,566,087 B2 | 2/2017 | Bierman et al. |
| 9,675,784 B2 | 6/2017 | Belson |
| 9,713,695 B2 | 7/2017 | Bunch et al. |
| 9,764,117 B2 | 9/2017 | Bierman et al. |
| 9,770,573 B2 | 9/2017 | Golden et al. |
| 9,814,861 B2 | 11/2017 | Boutillette et al. |
| 9,820,845 B2 | 11/2017 | von Lehe et al. |
| 9,861,383 B2 | 1/2018 | Clark |
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 | 3/2018 | Tal et al. |
| 9,950,139 B2 | 4/2018 | Blanchard et al. |
| 9,981,113 B2 | 5/2018 | Bierman |
| 10,010,312 B2 | 7/2018 | Tegels |
| 10,065,020 B2 | 9/2018 | Gaur |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,806,901 B2 | 10/2020 | Burkholz et al. |
| 2001/0044594 A1 | 11/2001 | Martin et al. |
| 2002/0040231 A1 | 4/2002 | Wysoki |
| 2002/0107506 A1 | 8/2002 | McGuckin et al. |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |

(56)                   References Cited

U.S. PATENT DOCUMENTS

| | | |
|---|---|---|
| 2003/0100849 A1 | 5/2003 | Jang |
| 2003/0153874 A1 | 8/2003 | Tal |
| 2003/0158514 A1 | 8/2003 | Tal |
| 2004/0116901 A1 | 6/2004 | Appling |
| 2004/0193093 A1 | 9/2004 | Desmond |
| 2004/0230178 A1 | 11/2004 | Wu |
| 2005/0004554 A1 | 1/2005 | Osborne |
| 2005/0049552 A1 | 3/2005 | Holzapfel et al. |
| 2005/0245882 A1 | 11/2005 | Elkins et al. |
| 2005/0245887 A1 | 11/2005 | Olsen et al. |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2008/0039796 A1 | 2/2008 | Nakajima |
| 2008/0045894 A1 | 2/2008 | Perchik et al. |
| 2008/0125744 A1 | 5/2008 | Treacy |
| 2008/0125748 A1 | 5/2008 | Patel |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2009/0093670 A1 | 4/2009 | Annest et al. |
| 2009/0221961 A1 | 9/2009 | Tal et al. |
| 2009/0270889 A1 | 10/2009 | Tal et al. |
| 2010/0256487 A1 | 10/2010 | Hawkins et al. |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0144620 A1 | 6/2011 | Tal |
| 2011/0152836 A1 | 6/2011 | Riopelle et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0209221 A1 | 8/2012 | Patterson et al. |
| 2012/0220942 A1 | 8/2012 | Hall et al. |
| 2012/0283640 A1 | 11/2012 | Anderson et al. |
| 2012/0316500 A1 | 12/2012 | Bierman et al. |
| 2013/0012924 A1 | 1/2013 | Davis et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0094741 A1 | 4/2014 | Bellisario et al. |
| 2014/0100552 A1 | 4/2014 | Gallacher et al. |
| 2014/0155863 A1 | 6/2014 | Walker et al. |
| 2014/0180255 A1 | 6/2014 | LeBlanc et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0080939 A1 | 3/2015 | Adams et al. |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Barnell |
| 2016/0114124 A1 | 4/2016 | Tal |
| 2016/0220786 A1 | 8/2016 | Mitchell et al. |
| 2016/0220795 A1 | 8/2016 | Korkuch et al. |
| 2016/0325073 A1 | 11/2016 | Davies et al. |
| 2016/0338728 A1 | 11/2016 | Tal |
| 2016/0346503 A1 | 12/2016 | Jackson et al. |
| 2017/0035989 A1 | 2/2017 | Gilman |
| 2017/0035990 A1 | 2/2017 | Swift |
| 2017/0072165 A1 | 3/2017 | Lim et al. |
| 2017/0120000 A1 | 5/2017 | Osypka et al. |
| 2017/0128700 A1 | 5/2017 | Roche Rebollo |
| 2017/0172653 A1 | 6/2017 | Urbanski et al. |
| 2017/0239443 A1 | 8/2017 | Abitabilo et al. |
| 2017/0273713 A1 | 9/2017 | Shah et al. |
| 2017/0296792 A1 | 10/2017 | Ornelas Vargas et al. |
| 2017/0326339 A1 | 11/2017 | Bailey et al. |
| 2017/0333681 A1 | 11/2017 | Di Caprio et al. |
| 2017/0361070 A1 | 12/2017 | Hivert |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0193042 A1 | 7/2018 | Wilson et al. |
| 2018/0296799 A1 | 10/2018 | Horst et al. |
| 2018/0296804 A1 | 10/2018 | Bierman |
| 2018/0339131 A1 | 11/2018 | Muse et al. |
| 2019/0015646 A1 | 1/2019 | Matlock et al. |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0255294 A1 | 8/2019 | Mitchell et al. |
| 2019/0276268 A1 | 9/2019 | Akingba |
| 2019/0321590 A1 | 10/2019 | Burkholz et al. |
| 2020/0016374 A1 | 1/2020 | Burkholz et al. |
| 2020/0030124 A1 | 1/2020 | Bluecher et al. |
| 2020/0094025 A1 | 3/2020 | Wisman |
| 2021/0069471 A1 | 3/2021 | Howell |
| 2021/0121661 A1* | 4/2021 | Howell ............. A61M 25/0045 |
| 2021/0121667 A1 | 4/2021 | Howell |
| 2021/0187245 A1 | 6/2021 | Ishida |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001138 A1 | 1/2022 | Howell |
| 2022/0032013 A1 | 2/2022 | Howell et al. |
| 2022/0040447 A1 | 2/2022 | Mewissen |
| 2023/0126869 A1 | 4/2023 | Sepulveda et al. |
| 2023/0233796 A1 | 7/2023 | Howell |
| 2023/0233800 A1 | 7/2023 | Howell et al. |
| 2024/0091501 A1 | 3/2024 | Howell |
| 2024/0181210 A1 | 6/2024 | Howell et al. |
| 2024/0198042 A1 | 6/2024 | Sepulveda |

FOREIGN PATENT DOCUMENTS

| | | |
|---|---|---|
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |
| EP | 2512576 A2 | 10/2012 |
| EP | 2152348 B1 | 2/2015 |
| EP | 3093038 B1 | 5/2019 |
| EP | 2260897 B1 | 9/2019 |
| ES | 2303546 T3 | 8/2008 |
| GB | 1273547 A | 5/1972 |
| WO | 94/21315 A1 | 9/1994 |

(56) References Cited

FOREIGN PATENT DOCUMENTS

| WO | 95/32009 | A2 | 11/1995 |
|----|----------|----|---------|
| WO | 98/44979 | A1 | 10/1998 |
| WO | 98/53871 | A1 | 12/1998 |
| WO | 99/12600 | A1 | 3/1999 |
| WO | 99/26681 | A1 | 6/1999 |
| WO | 2003008020 | A1 | 1/2003 |
| WO | 2003057272 | A2 | 7/2003 |
| WO | 2003066125 | A2 | 8/2003 |
| WO | 2004037331 | A1 | 5/2004 |
| WO | 2006055288 | A2 | 5/2006 |
| WO | 2006055780 | A2 | 5/2006 |
| WO | 2007046850 | A2 | 4/2007 |
| WO | 2008033983 | A1 | 3/2008 |
| WO | 2008092029 | A2 | 7/2008 |
| WO | 2008/131300 | A2 | 10/2008 |
| WO | 2008131289 | A2 | 10/2008 |
| WO | 2009114833 | A1 | 9/2009 |
| WO | 2009114837 | A2 | 9/2009 |
| WO | 2010/048449 | A2 | 4/2010 |
| WO | 2010056906 | A2 | 5/2010 |
| WO | 2010083467 | A2 | 7/2010 |
| WO | 2010/132608 | A2 | 11/2010 |
| WO | 2011081859 | A2 | 7/2011 |
| WO | 2011097639 | A2 | 8/2011 |
| WO | 2011146764 | A1 | 11/2011 |
| WO | 2012068162 | A2 | 5/2012 |
| WO | 2012068166 | A2 | 5/2012 |
| WO | 2012135761 | A1 | 10/2012 |
| WO | 2012162677 | A1 | 11/2012 |
| WO | 2013026045 | A1 | 2/2013 |
| WO | 2013138519 | A1 | 9/2013 |
| WO | 2014006403 | A1 | 1/2014 |
| WO | 2014/100392 | A1 | 6/2014 |
| WO | 2014113257 | A2 | 7/2014 |
| WO | 2014152005 | A2 | 9/2014 |
| WO | 2014197614 | A2 | 12/2014 |
| WO | 2015057766 | A1 | 4/2015 |
| WO | 2016110824 | A1 | 7/2016 |
| WO | 2016123278 | A1 | 8/2016 |
| WO | 2016139590 | A1 | 9/2016 |
| WO | 2016139597 | A2 | 9/2016 |
| WO | 2016176065 | A1 | 11/2016 |
| WO | 2018089275 | A1 | 5/2018 |
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019/146026 | A1 | 8/2019 |
| WO | 2019199734 | A1 | 10/2019 |
| WO | 2020069395 | A1 | 4/2020 |
| WO | 2021050302 | A1 | 3/2021 |
| WO | 2021/077103 | A1 | 4/2021 |
| WO | 2021062023 | A1 | 4/2021 |
| WO | 2021081205 | A1 | 4/2021 |
| WO | 2021086793 | A1 | 5/2021 |
| WO | 2023069553 | A2 | 4/2023 |
| WO | 2023081314 | A1 | 5/2023 |
| WO | 2023141112 | A1 | 7/2023 |
| WO | 2023146773 | A3 | 9/2023 |
| WO | 2024123925 | A2 | 6/2024 |
| WO | 2024129815 | A1 | 6/2024 |

OTHER PUBLICATIONS

PCT/US2023/083764 filed Dec. 13, 2023 International Search Report and Written Opinion dated Apr. 22, 2024.

U.S. Appl. No. 17/363,500, filed Jun. 30, 2021 Restriction Requirement dated Jul. 16, 2024.

U.S. Appl. No. 17/363,500, filed Jun. 30, 2021 Final Office Action dated Feb. 20, 2025.

U.S. Appl. No. 17/363,500, filed Jun. 30, 2021 Non-Final Office Action dated Sep. 4, 2025.

U.S. Appl. No. 17/969,626, filed Oct. 19, 2022 Non-Final Office Action dated Sep. 25, 2025.

U.S. Appl. No. 18/076,169, filed Dec. 6, 2022 Non-Final Office Action dated Aug. 8, 2025.

U.S. Appl. No. 18/076,169, filed Dec. 6, 2022 Notice of Allowance dated Dec. 5, 2025.

U.S. Appl. No. 18/081,480, filed Dec. 14, 2022 Non-Final Office Action dated Sep. 17, 2025.

U.S. Appl. No. 18/098,052, filed Jan. 17, 2023 Restriction Requirement dated Dec. 5, 2025.

U.S. Appl. No. 18/098,059, filed Jan. 17, 2023 Restriction Requirement dated Nov. 20, 2025.

PCT/US2020/048583 filed Aug. 28, 2020 International Search Report and Written Opinion dated Nov. 13, 2020.

PCT/US2020/052536 filed Sep. 24, 2020 International Search Report and Written Opinion dated Dec. 4, 2020.

PCT/US2020/056364 filed Oct. 19, 2020 International Search Report and Written Opinion dated Jan. 19, 2021.

PCT/US2020/056864 filed Oct. 22, 2020 International Search Report and Written Opinion dated Jan. 14, 2021.

PCT/US2020/057202 filed Oct. 23, 2020 International Search Report and Written Opinion dated Jan. 21, 2021.

PCT/US2020/057397 filed Oct. 26, 2020 International Search Report and Written Opinion dated Mar. 10, 2021.

PCT/US2021/014700 filed Jan. 22, 2021 International Search Report and Written Opinion dated Jun. 29, 2021.

PCT/US2021/028018 filed Apr. 19, 2021 International Search Report and Written Opinion dated Sep. 13, 2021.

PCT/US2021/028683 filed Apr. 22, 2021 International Search Report and Written Opinion dated Sep. 16, 2021.

PCT/US2021/029183 filed Apr. 26, 2021 International Search Report and Written Opinion dated Sep. 24, 2021.

PCT/US2021/033443 filed May 20, 2021 International Search Report and Written Opinion dated Sep. 23, 2021.

PCT/US2021/039084 filed Jun. 25, 2021 International Search Report and Written Opinion dated Jan. 10, 2022.

PCT/US2021/039843 filed Jun. 30, 2021 International Search Report and Written Opinion dated Nov. 11, 2021.

PCT/US2021/044029 filed Jul. 30, 2021 International Search Report and Written Opinion dated Dec. 9, 2021.

U.S. Appl. No. 15/008,628, filed Jan. 28, 2016 Final Office Action dated May 30, 2018.

U.S. Appl. No. 15/008,628, filed Jan. 28, 2016 Non-Final Office Action dated Jan. 25, 2019.

U.S. Appl. No. 15/008,628, filed Jan. 28, 2016 Non-Final Office Action dated Nov. 2, 2017.

U.S. Appl. No. 15/008,628, filed Jan. 28, 2016 Notice of Allowance dated May 15, 2019.

U.S. Appl. No. 16/398,020, filed Apr. 29, 2019 Final Office Action dated Jan. 25, 2022.

U.S. Appl. No. 16/398,020, filed Apr. 29, 2019 Non-Final Office Action dated May 11, 2021.

U.S. Appl. No. 17/006,553, filed Aug. 28, 2020 Final Office Action dated Sep. 28, 2022.

U.S. Appl. No. 17/006,553, filed Aug. 28, 2020 Non-Final Office Action dated Mar. 16, 2022.

U.S. Appl. No. 17/077,728, filed Oct. 22, 2020 Non-Final Office Action dated Feb. 9, 2022.

PCT/US2023/082753 filed Dec. 6, 2023 International Search Report and Written Opinion dated May 29, 2024.

U.S. Appl. No. 17/363,500, filed Jun. 30, 2021 Non-Final Office Action dated Sep. 23, 2024.

PCT/US2022/047179 filed Oct. 19, 2022 International Search Report and Written Opinion dated Apr. 18, 2023.

PCT/US2022/048881 filed Nov. 3, 2022 International Search Report and Written Opinion dated Mar. 31, 2023.

PCT/US2023/010972 filed Jan. 17, 2023 International Search Report and Written Opinion dated May 30, 2023.

EP 20862936.0 filed Mar. 28, 2022 Extended European Search Report dated Sep. 19, 2023.

PCT/US2023/010971 filed Jan. 17, 2023 International Search Report and Written Opinion dated Jul. 28, 2023.

(56)        References Cited

OTHER PUBLICATIONS

U.S. Appl. No. 17/006,553, filed Aug. 28, 2020 Non-Final Office Action dated Jun. 26, 2023.
U.S. Appl. No. 17/006,553, filed Aug. 28, 2020 Notice of Allowance dated Sep. 11, 2023.
Yamada, T. et al., "Selective Hemi-Portocaval Shunt Based on Portal Vein Pressure for Small-for-Size Graft in Adult Living Donor Liver Transplantation." American Journal of Transplantation, Blackwell Munksgaard, DK, vol. 8, No. 4, Feb. 5, 2008 [Feb. 5, 2008] pp. 847-853.
U.S. Appl. No. 17/363,500, filed Jun. 30, 2021 Notice of Allowance dated Jan. 27, 2026.
U.S. Appl. No. 17/969,626, filed Oct. 19, 2022 Notice of Allowance dated Jan. 27, 2026.
U.S. Appl. No. 18/081,480, filed Dec. 14, 2022 Final Office Action dated Mar. 30, 2026.
U.S. Appl. No. 18/098,052, filed Jan. 17, 2023 Non-Final Office Action dated Feb. 23, 2026.
U.S. Appl. No. 18/098,059, filed Jan. 17, 2023 Ex Parte Quayle Action dated Mar. 26, 2026.
U.S. Appl. No. 18/524,480, filed Nov. 30, 2023 Non-Final Office Action dated Mar. 25, 2026.

* cited by examiner

SECTION A

SECTION B

SECTION C

SECTION D

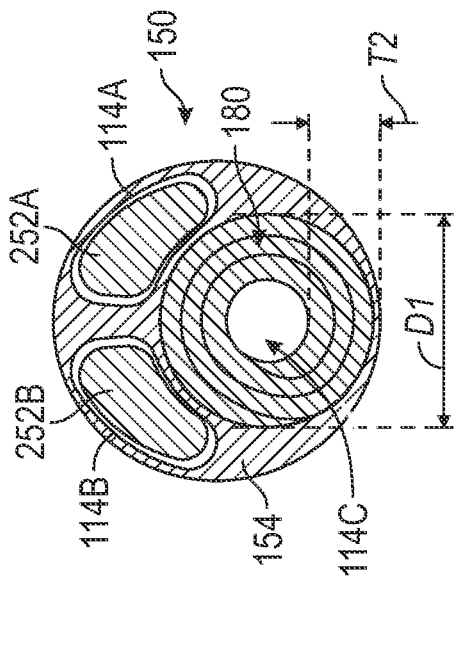
FIG. 7E
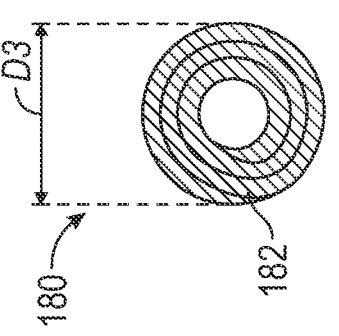
FIG. 7D
FIG. 7C
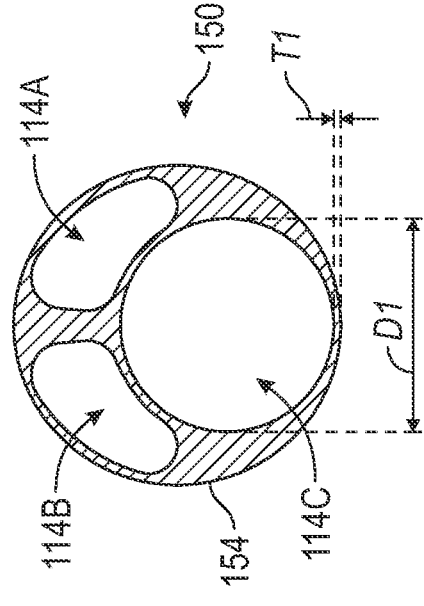
FIG. 7A
FIG. 7B

REINFORCED CATHETER TIP VIA ROLLER EXTRUSION

PRIORITY

This application claims the benefit of priority to U.S. Provisional Application No. 63/275,768, filed Nov. 4, 2021, which is incorporated by reference in its entirety into this application.

BACKGROUND

Rapidly Insertable Central Catheter (RICC) systems include a catheter having a first section disposed distally, defining a single lumen, and having a first outer diameter, a second section disposed proximally, defining two or more lumen, and having a second diameter larger than the first diameter, and a transition section disposed therebetween and extending from the first outer diameter of the first section to the second outer diameter of the second section. The configuration of the RICC catheter allows a clinician to access the vasculature with the first section, dilate the access site with the transition section, and place the second section at a target location within the vasculature in a single step, mitigating the introduction and removal of multiple tools to achieve each of these steps separately.

Forming the RICC catheter requires coupling the three different structures of the first section, the transition section, and the second section together, while maintaining a smooth outer profile. Each of the three different structures are required to display different mechanical properties to fulfil the respective roles in the placement process. However, smaller gauge catheters provide thinner walls and as such provide a smaller surface area with which to couple the three different structures together. "Tipping" thin walled catheters can be challenging since the thin wall and small cross sectional area provides very little material with which to couple the structures together and can be susceptible to failure of the device either during manufacture or during use. Embodiments disclosed herein are directed to address the foregoing.

SUMMARY

Briefly summarized, embodiments disclosed herein are directed to distal tip structures for a catheter, such as a RICC, and associated methods of manufacture. Disclosed herein is a method of forming a catheter including, extruding a proximal section of a catheter body having a first catheter lumen and a second catheter lumen, coupling a distal tip structure to the proximal section including, placing a spiral plug in a rolled configuration within the first catheter lumen, placing a plug within the second catheter lumen, a distal tip of the plug aligned with a distal end of the second catheter lumen, aligning a lumen of the distal tip structure with the first catheter lumen, and coupling the proximal end of the distal tip structure with the distal end of the proximal section.

In some embodiments, the method further includes forming the spiral plug, including, providing a tube having an outer diameter equal to or greater than an inner diameter of the first catheter lumen, cutting the tube longitudinally, and rolling the tube into a spiral configuration, having an outer diameter equal to or less than the inner diameter of the first catheter lumen. In some embodiments, the spiral plug engages the first catheter lumen in an interference fit. In some embodiments, coupling the proximal end of the distal tip structure with the distal end of the proximal section includes adhering, bonding, or welding the distal tip structure with the proximal section.

In some embodiments, coupling the proximal end of the distal tip structure with the distal end of the proximal section includes adhering, bonding, or welding the spiral plug to an inner surface of the first catheter lumen and to one or both of the distal tip structure and the proximal section. In some embodiments, the method further includes boring out a portion of the first catheter lumen adjacent the spiral plug. In some embodiments, the distal tip structure is formed of a first material, the proximal section is formed of a second material, and the spiral plug is formed of a third material, the second material being different from one or both of the first material and the third material.

In some embodiments, the second material includes a more compliant, or softer durometer, mechanical properties relative to the first material. In some embodiments, the distal tip structure includes one or both of a first section and a transition section. In some embodiments, the first section defines a single lumen and defines an outer diameter that is less than an outer diameter of the proximal section. In some embodiments, the transition section defines a tapered outer profile extending from the outer diameter of the first section to the outer diameter of the proximal section.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 7A shows a distal end view of a second section of the catheter of FIG. 1B, in accordance with embodiments disclosed herein.

FIGS. 7B-7D show an exemplary method of forming a spiral plug, in accordance with embodiments disclosed herein.

FIG. 7E shows a distal end view of a second section of a catheter including a spiral plug disposed in a lumen thereof, in accordance with embodiments disclosed herein.

DESCRIPTION

Figure 1A:
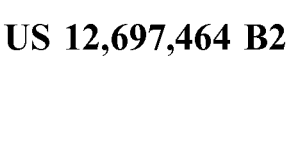
FIG. 1A shows a perspective view of a catheter placement system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

To assist in the description of embodiments described herein, as shown in FIG. 1A, a longitudinal axis extends substantially parallel to an axial length of the catheter. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

Figure 1B:
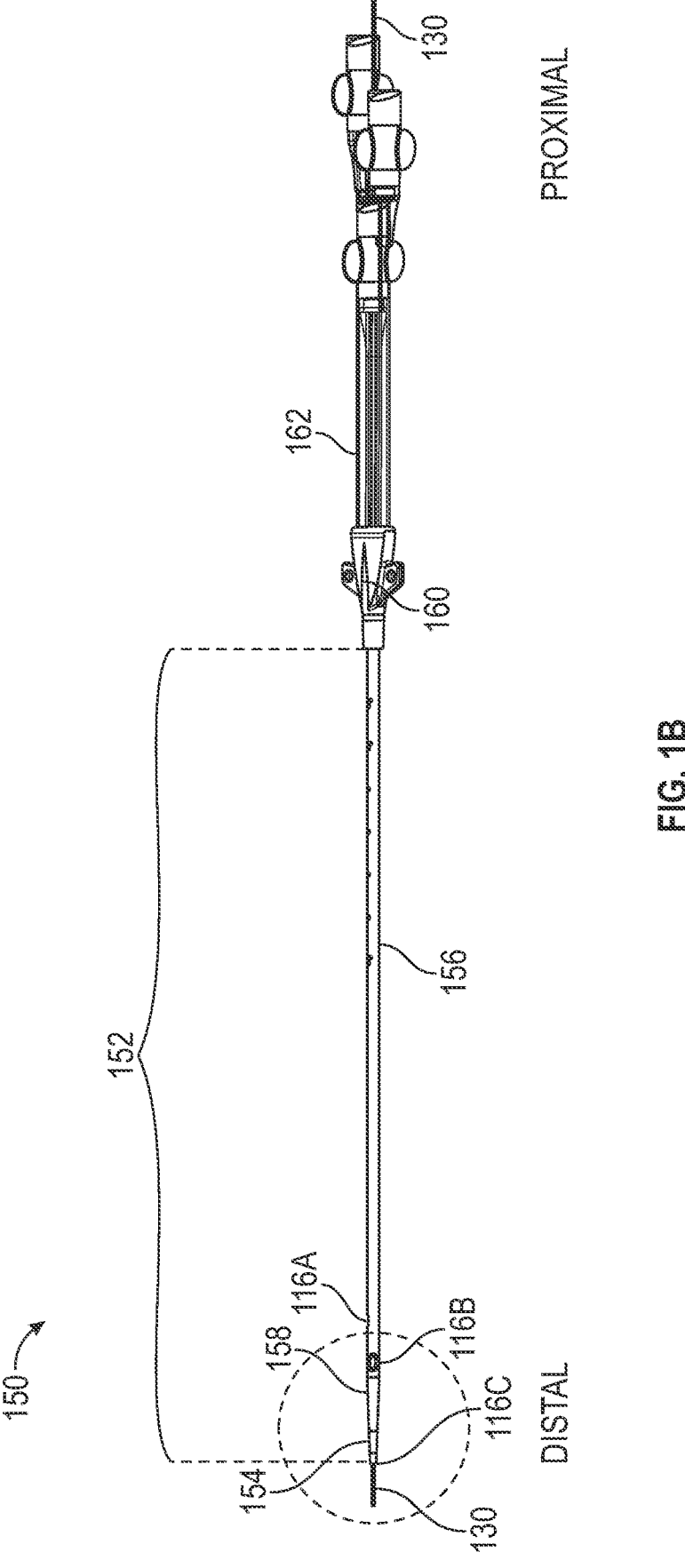
FIG. 1B shows a side view of a catheter of the catheter placement system of FIG. 1A, in accordance with embodiments disclosed herein.

FIGS. 1A-1B show details of an exemplary catheter placement system ("placement system") 100 generally including a needle 120, a guidewire 130, a syringe system 140, and a catheter 150. In an embodiment the catheter placement system 100 can be a Rapidly Insertable Central Catheter (RICC) placement system 100. However, it will be appreciated that other catheter placement systems configured to place other types of catheters are also contemplated. Exemplary catheters can also include peripheral intravenous (PIV) catheters, peripherally inserted central catheter (PICC), central venous catheters (CVC), midline catheters, dialysis catheters, single lumen catheters, multi-lumen catheters, or the like.

In an embodiment, the catheter 150 can generally include a catheter body 152 supported at a proximal end by a catheter hub ("hub") 160. The hub 160 can include one or more extension legs 162 extending proximally therefrom. Each extension leg of the one or more extension legs 162 can be in fluid communication with a lumen of the catheter body 152. The catheter body 152 can include a first section 154 disposed distally, a second section 156 disposed proximally, and a transition section 158 disposed therebetween. The first section 154 can define a single lumen and have a first outer diameter, the second section 156 can define two or more lumen and can have a second diameter larger than the first diameter. The transition section 158 disposed between the first section 154 and the second section 156 can define a tapered abluminal shape extending from the first diameter of the first section to the second diameter of the second section. A guidewire 130 can extend through a lumen of the catheter 150 from a proximal end of an extension leg 162, to a distal tip of the first section 154.

In an exemplary method of use for the catheter placement system 100 to place the catheter 150, the needle 120 can be urged distally into the patient and access a vasculature, forming an insertion site. A syringe system 140, or similar device can draw a fluid flow proximally through a needle lumen 122 to observe a color or pulsatile flow and confirm correct vascular access. Once correct vascular access has been confirmed, the guidewire 130 can then be advanced through the needle lumen 122 and into the vasculature to maintain patency of the insertion site. The needle 120 and syringe system 140 assembly can then be withdrawn proximally. In an embodiment, a distal tip of the guidewire 130 can reside within the needle lumen 122 during venipuncture, which can expedite accessing the vasculature once venous access is confirmed and maintain patency of the insertion site.

The catheter 150 can then be advanced over the guidewire 130 and into the vasculature. The first section 154 of the catheter 150, having only a single lumen and defining a relatively smaller outer diameter, can enter the vasculature over the guidewire 130, anchoring the insertion site. The transition section 158 can then dilate the insertion site to allow the relatively larger diameter second section 156, defining two or more lumen, to enter the vasculature. Once the catheter 150 has been placed, the guidewire 130 can be withdrawn proximally. Further details and embodiments of RICC systems 10 can be found, for example, in U.S. Pat. No. 10,376,675, U.S. 2019/0255294, U.S. 2021/0069471, U.S.

2021/0085927, U.S. 2021/0113809, U.S. 2021/0113810, U.S. 2021/0121661, U.S. 2021/0228843, U.S. 2021/0283368, U.S. 2021/0283381, U.S. 2021/0322729, U.S. 2021/0330941, U.S. 2021/0330942, U.S. 2021/0361915, U.S. 2021/0379336, U.S. 2021/0402142, U.S. 2021/0402149, U.S. 2021/0402153, U.S. 2021/0121667, U.S. 2022/0001138, U.S. 2022/0032013, U.S. 2022/0032014, U.S. 2022/0062528, U.S. 2022/0126064, U.S. 2022/0152368, U.S. 2022/0176081, U.S. 2022/0176082, U.S. 2022/0193376, U.S. 2022/0193377, U.S. 2022/0193378, U.S. 2022/0193379, and U.S. 2022/0296862, each of which is incorporated by reference in its entirety into this application.

As set forth herein, different sections of the catheter 150 are required to perform different functions and as such are required to display different mechanical properties. For example, the first section 154 and/or the transition section 158 can provide a more rigid mechanical properties or harder durometer material relative to the second section 156. As such, the first section 154 and/or transition section 158 can withstand greater axial forces without kinking or collapsing, as theses sections are urged distally forming and dilating the insertion site. The second section 156 can be formed of a softer durometer, or a more compliant material to facilitate negotiating the second section 156 through tortuous vascular pathways. Forming the catheter 150 requires the coupling together of these different structures, formed of different materials, while maintaining a smooth abluminal surface.

Figure 2:
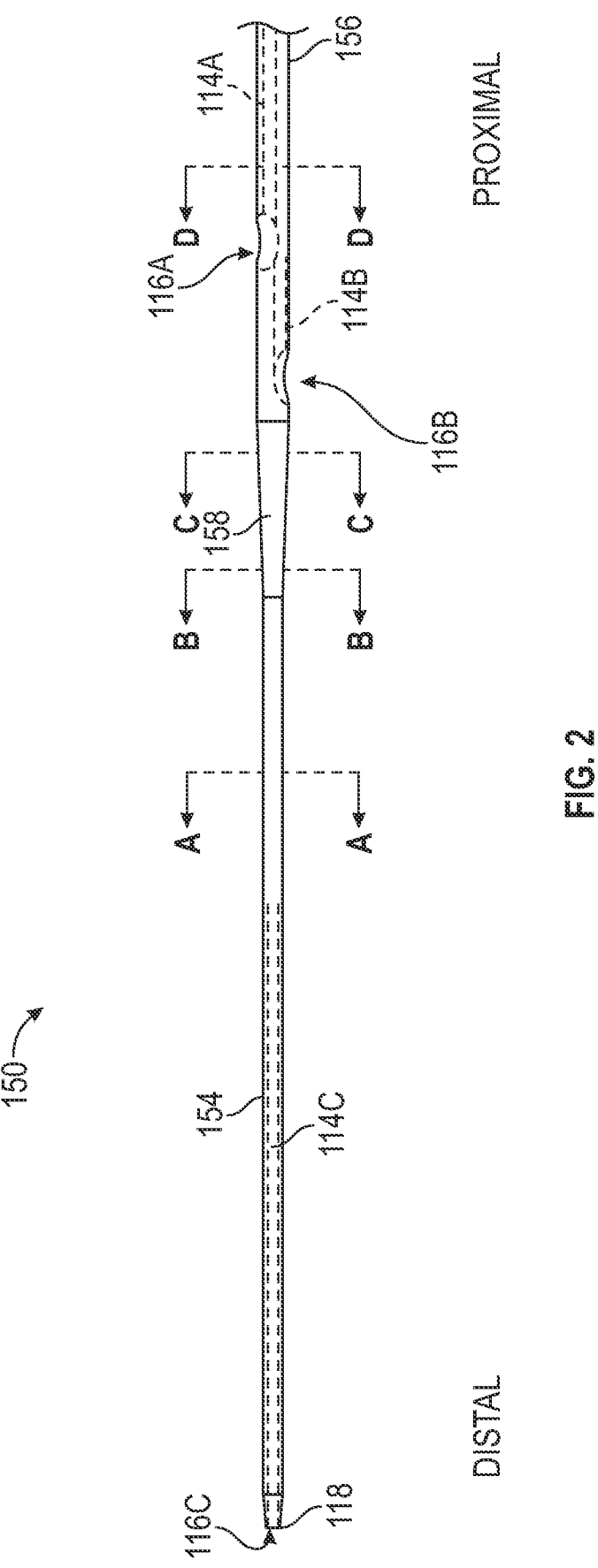
FIG. 2 shows close up detail of a distal portion of the catheter of FIG. 1B, in accordance with embodiments disclosed herein.

FIG. 2 shows further details of a distal portion of the catheter 150, including the first section 154, the second section 156, and the transition section 158. In an embodiment, the second section 156 can include a proximal lumen 114A terminating at a proximal lumen aperture 116A, and a medial lumen 114B terminating at a medial lumen aperture 116B. Each of the proximal lumen aperture 116A and the medial lumen aperture 116B can extend through a side wall of the second section 156. Each of the proximal lumen aperture 116A and the medial lumen aperture 116B can be disposed proximally of the transition section 158. In an embodiment, the proximal lumen aperture 116A can be disposed proximally of the medial lumen aperture 116B. In an embodiment, the proximal lumen aperture 116A and the medial lumen aperture 116B can be disposed equidistant from a distal tip 118 of the catheter 150. A distal lumen 114C of the catheter 150 can extend to a distal tip 118 of the catheter 150 and can communicate with a distal lumen aperture 116C

Figure 3:
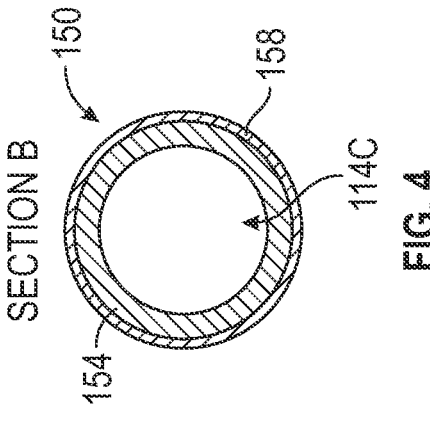
FIGS. 3-6 show various cross-sectional views of the distal portion of FIG. 2, in accordance with embodiments disclosed herein.
Figure 4:
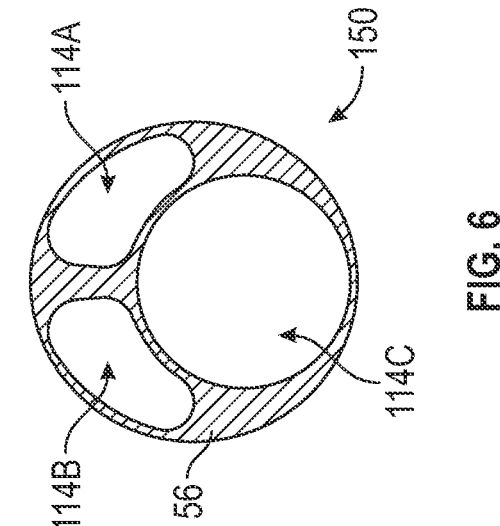
Figure 5:
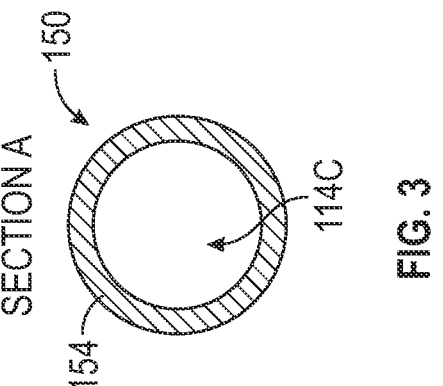
Figure 6:
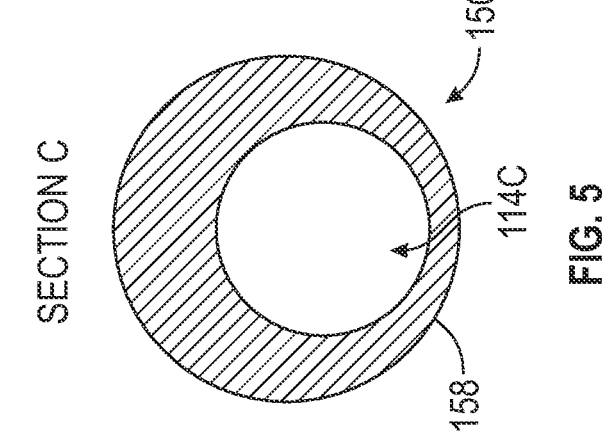

FIG. 3 shows a cross section view of the first section 154 at point "A" of FIG. 2. As shown, the first section 154 can define a single lumen and a relatively smaller outer diameter. FIG. 4 shows a cross section view of the junction between the first section 154 and the transition section 158, at point "B" of FIG. 2, where a portion of the first section 154 is received within the transition section 158. FIG. 5 shows a cross section view of the transition section 158 at point "C" of FIG. 2, where an axis of the distal lumen 114C is offset from an axis of the transition section 158 as the distal lumen 114 transitions between the first section 154 and the second section 156. FIG. 6 shows a cross section view of the second section 156 at point "D" of FIG. 2, showing the proximal lumen 114A, the medial lumen 114B and the distal lumen 114C.

Tip Forming Methods

Figures 8A, 8B:
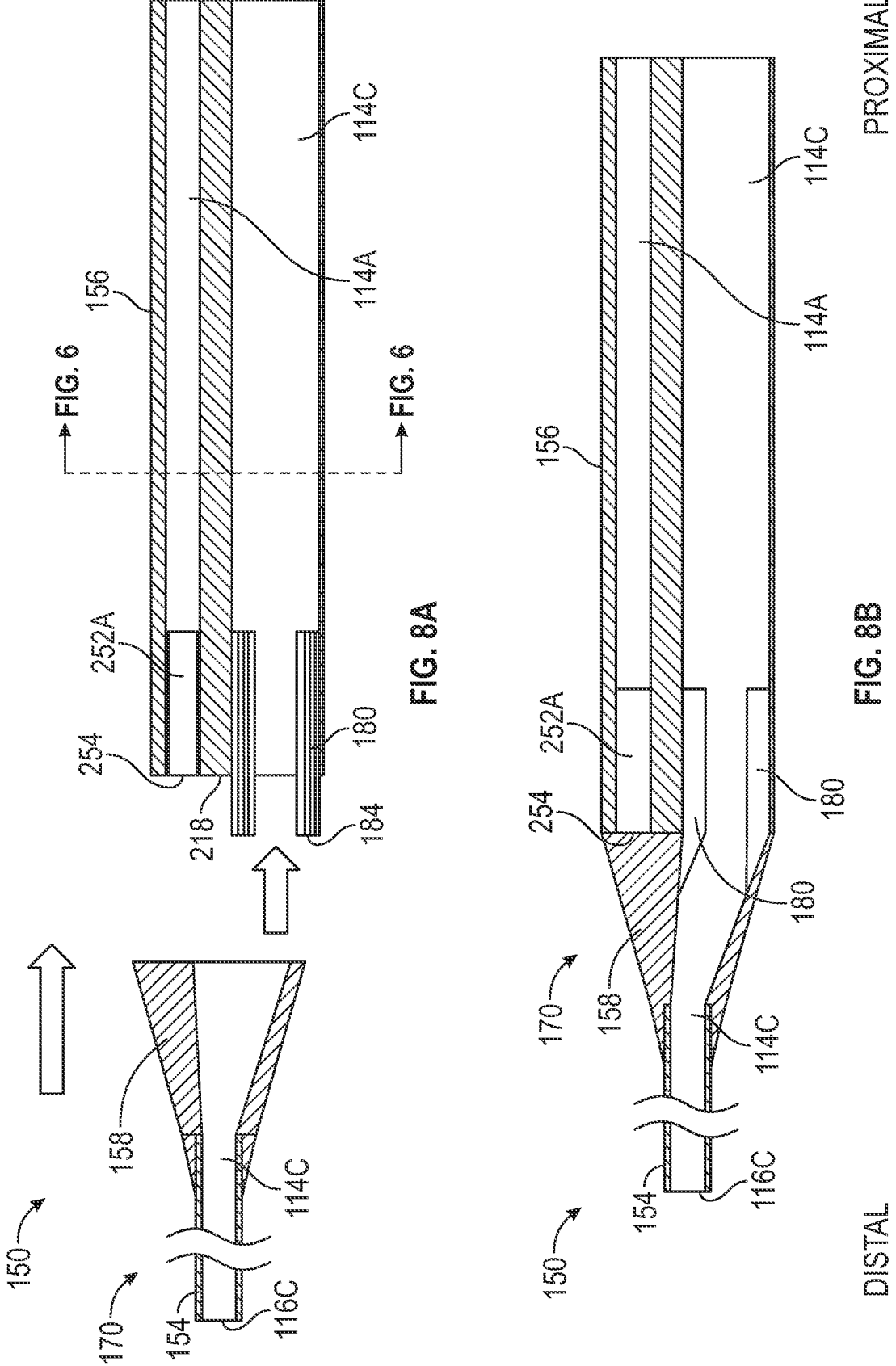
FIGS. 8A-8C show an exemplary method of coupling a distal tip structure with a second section of a catheter, in accordance with embodiments disclosed herein.
Figure 8C:
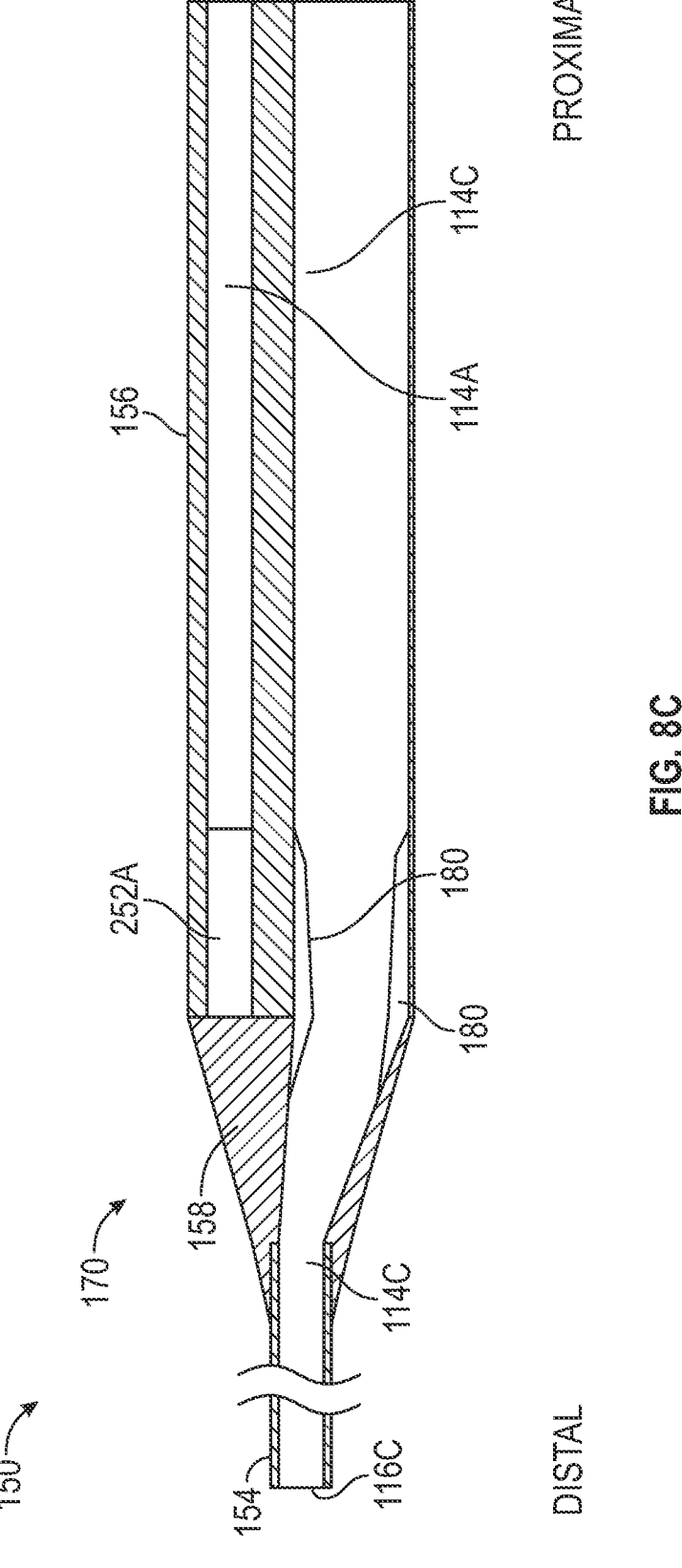

FIGS. 7A-8C show an exemplary method of manufacturing a catheter 150 including coupling a distal tip structure 170 to a second section 156 to form a catheter body 152. In an embodiment, the distal tip structure 170 includes one or both of the transition section 158 and at least a portion of the first section 154. In an exemplary method of coupling the distal tip structure 170 to a second section 156, termed "tipping," the second section 156 can be formed having one or more lumen 114. In an embodiment, the second section 156 can be extruded and trimmed to a desired length. It will be appreciated, however, that other methods of forming the second section 156 are also contemplated. As shown in FIGS. 7A-8C, a triple lumen second section 156 is provided including a first (proximal) lumen 114A, a second (medial) lumen 114B, and a third (distal) lumen 114C. However, it will be appreciated that other single or multi-lumen second sections 156, or catheters 150, are also contemplated. To note, the lumen 114A, 114B, 114C of the catheter body 152 can be arranged radially about a central axis of the second section 156, as shown in FIGS. 6-7A. To note, FIGS. 8A-8C show a longitudinal cross-section of the second section 156 with the medial lumen 114B disposed behind the proximal lumen 114A, and the distal lumen 114C.

In an embodiment, a plug 252 can be disposed into one or both of the proximal lumen 114A and the medial lumen 114B. For example, a first plug 252A can be disposed within a distal end of a first lumen 114A, and a second plug 252B can be disposed within a distal end of a second lumen 114B. A distal tip 254 of the plug 252 can align with a distal end 218 of the second section 156. Optionally, a distal tip 254 of the plug 252 can be trimmed to align with a distal end 218 of the second section 156.

As shown in FIG. 7A, with increasingly smaller gauged catheters, portions of a wall of the catheter 150 can provide a reduced thickness, e.g. thickness (T1). As such, a cross-sectional area of these thinned portions of the catheter wall can provide very little surface area for coupling a distal structure 170 thereto. As such, the joint at these areas can be weakened and potentially fail. Alternatively, the wall of second section 156 can misalign with a wall of the distal tip structure 170 causing failure during manufacture. In an embodiment, a spiral plug 180 can be provided to facilitate coupling the distal tip structure 170 with the second section 156.

As shown in FIGS. 7B-7D, the spiral plug 180 can be formed by providing a tube 182 having an outer diameter (D2) equal to or greater than an inner diameter (D1) of a lumen of the second section 156, e.g. a distal lumen 114C. The tube 182 can be cut longitudinally (FIG. 7C) and the tube 182 can be rolled in to a spiral configuration (FIG. 7D) having an outer diameter (D3) equal to or less than the inner diameter (D1) of the lumen 114. A proximal portion of the spiral plug 180 can be placed within the lumen 114. In an embodiment, a distal end 184 of the spiral plug 180 can extend distally of the distal end 218 of the second section 156. In an embodiment, a distal end 184 of the spiral plug 180 can align flush with the distal end 218 of the second section 156. Optionally, the distal end 184 of the spiral plug 180 can be trimmed to align flush with the distal end 218 of the second section 156.

In an embodiment, the spiral plug 180 can be biased towards the unrolled configuration (FIG. 7C). As such, when placed within the lumen 114, the spiral plug 180 can unroll from the rolled configuration (FIG. 7D) and engage the lumen 114 in an interference fit. In an embodiment, the spiral plug 180 can be coupled to an inner surface of the lumen 114 using adhesive, bonding, welding, or the like. Advantageously, the spiral plug 180 can co-operate with the wall of the second section 156 to provide a greater wall thickness (T2) to facilitate coupling a distal tip structure 170 thereto.

FIG. 8A shows a longitudinal cross-section view of the second section 156 including a first plug 252A placed in the proximal lumen 114A. While not shown in FIG. 8A, a second plug 252B can be placed in the medial lumen 114B, as described herein. Further, a spiral plug 180 is placed in the distal lumen 114C. A distal tip structure 170 can then be coupled with a distal end 218 of the second section 156, for example using adhesive, bonding, solvent bonding, welding, or the like. In an embodiment, the spiral plug 180 can facilitate aligning a lumen of the distal tip structure 170 with a lumen 114 of the second section 156 to form the distal lumen 114C extending to a distal lumen aperture 116C.

In an embodiment, a first plug 252A can seal the proximal lumen 114A, and the second plug 252B can seal the medial lumen 114B, proximally of the transition section 158. The proximal lumen aperture 116A can then be formed through a wall of the catheter body 152 and communicate with the proximal lumen 114A. The medial lumen aperture 116B can then be formed through a wall of the catheter body 152 and communicate with the medial lumen 116B.

In an embodiment, the spiral plug 180 can then be removed from the lumen 114 once the distal tip structure 170 is coupled to the second section 156. In an embodiment, the spiral plug 180 can be formed of a sacrificial material. During the tipping of the second section 156 with the distal structure 170, a portion of the spiral plug 180 can be melted and fused with an inner wall of the lumen 114 across the join between the second section 156 and the distal structure 170. As such, the spiral plug 180 can provide additional support across the join, ensuring a secure coupling. As shown in FIG. 8C, the bore of the spiral plug 180 can then be widened once the distal tip structure 170 has been coupled with the second section 156.

In an embodiment, one or both of the first section 154 and the transition section 158, i.e. the distal tip structure 170 can be formed of a first material, and the second section 156 can be formed of a second material. In an embodiment, the first material can display different mechanical properties from the second material. In an embodiment, one of the first material or the second material can be a plastic, polymer, polyurethane, composite, elastomer, or the like. In an embodiment, the first material can display more rigid, or harder durometer, mechanical properties relative to the second material that can display more compliant or softer durometer mechanical properties.

In an embodiment, the spiral plug 180 can be formed of the same material as one of a first material of the distal tip structure 170 or a second material of the second section 156. In an embodiment, the spiral plug 180 can be formed from a third material that can be different from both of the first material and the second material. In an embodiment, the third material can be a plastic, polymer, elastomer, polyurethane combinations thereof, or the like.

In an embodiment, the distal tip structure 170 can be coupled with the second section 156 by placing one or more of the distal end 218 of the second section 156, a plug 252, a spiral plug 180, and the distal tip structure 170 within a mold or die. Optionally a mandrel (not shown) can be placed within a portion of the distal lumen 114C. Energy (thermal, RF, ultrasonic welding, or the like) and/or pressure can be applied to the assembly within the die to melt or fuse the material of the distal end 218 of the second section 156, the plug 252, the spiral plug 180, and/or the distal tip structure 170 together to form the catheter body 152 of the catheter 150. The mandrel can define a portion of the distal lumen 114C extending therethrough and can be removed after the catheter body 152 has been formed.

In an embodiment, the distal tip structure 170 can define one or both of the transition section 158 and the first section 154. In an embodiment, the distal tip structure 170 can include the transition section 158 and can define a recess configured to receive a proximal end of the first section 154. The proximal end of the first section 154 can then be coupled with the transition section 158 using adhesive, bonding, welding, or the like. As such, the first section 154 can be formed of the third material, or of a fourth material different from that of the first, second, and third material.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A method of forming a catheter, comprising:
extruding a proximal section of a catheter body having a first catheter lumen and a second catheter lumen; and
coupling a distal tip structure to the proximal section, comprising:
placing a spiral plug in a rolled configuration within the first catheter lumen;
placing a plug within the second catheter lumen, a distal tip of the plug aligned with a distal end of the second catheter lumen;
aligning a lumen of the distal tip structure with the first catheter lumen; and
coupling a proximal end of the distal tip structure with the distal end of the proximal section.

2. The method according to claim 1, further including forming the spiral plug, comprising:
providing a tube having an outer diameter equal to or greater than an inner diameter of the first catheter lumen;
cutting the tube longitudinally; and
rolling the tube into a spiral configuration, having an outer diameter equal to or less than the inner diameter of the first catheter lumen.

3. The method according to claim 1, wherein the spiral plug engages the first catheter lumen in an interference fit.

4. The method according to claim 1, wherein coupling the proximal end of the distal tip structure with the distal end of the proximal section includes adhering, bonding, or welding the distal tip structure with the proximal section.

5. The method according to claim 1, wherein coupling the proximal end of the distal tip structure with the distal end of the proximal section includes adhering, bonding, or welding the spiral plug to an inner surface of the first catheter lumen and to one or both of the distal tip structure and the proximal section.

6. The method according to claim 1, further including boring out a portion of the first catheter lumen adjacent the spiral plug.

7. The method according to claim 1, wherein the distal tip structure is formed of a first material, the proximal section is formed of a second material, and the spiral plug is formed of a third material, the second material being different from one or both of the first material and the third material.

8. The method according to claim 7, wherein the second material includes a more compliant, or softer durometer, mechanical properties relative to the first material.

9. The method according to claim 1, wherein the distal tip structure includes one or both of a first section and a transition section.

10. The method according to claim 9, wherein the first section defines a single lumen and defines an outer diameter that is less than an outer diameter of the proximal section.

11. The method according to claim 10, wherein the transition section defines a tapered outer profile extending from the outer diameter of the first section to the outer diameter of the proximal section.

* * * * *